United States Patent [19]

Adler

[11] 4,020,831
[45] May 3, 1977

[54] BLOOD COLLECTING SYRINGE

[75] Inventor: Stanford L. Adler, Monsey, N.Y.

[73] Assignee: Technicon Instruments Corporation, Tarrytown, N.Y.

[22] Filed: Dec. 4, 1975

[21] Appl. No.: 637,506

[52] U.S. Cl. .......................... 128/2 F; 128/218 P; 128/219; 128/DIG. 5
[51] Int. Cl.[2] ......................................... A61B 5/14
[58] Field of Search .............. 128/2 F, DIG. 5, 220, 128/276, 278, 221, 218 P, 218 PA, 218 D, 218 DA, 218 R, 219

[56] References Cited
UNITED STATES PATENTS

| | | | |
|---|---|---|---|
| 977,952 | 12/1910 | Heilmann et al. | 128/220 |
| 2,495,027 | 1/1950 | Smith | 128/220 |
| 2,864,364 | 12/1958 | Mizzy | 128/220 |
| 3,098,482 | 7/1963 | O'Sullivan | 128/220 |
| 3,841,329 | 10/1974 | Killinger | 128/220 |
| 3,886,928 | 6/1975 | Sarstedt | 128/2 F |
| 3,886,930 | 6/1975 | Ryan | 128/2 F |
| 3,901,219 | 8/1975 | Kay | 128/2 F |
| 3,901,402 | 8/1975 | Ayres | 128/2 F X |

*Primary Examiner*—John D. Yasko
*Attorney, Agent, or Firm*—S. P. Tedesco

[57] ABSTRACT

An article for drawing a blood specimen comprising a specimen-receiving tube having a closed end and an open end, a resilient expandable plug received in the closed end portion of the tube in normally relatively light sealing engagement with the side wall structure of the tube, and an elongated cannula holder having a through longitudinal passageway for communication with the interior of the cannula, the plug and the holder having co-acting means for releasably coupling the plug and the holder when the holder passageway is in communication with the closed end portion of the tube through the plug, the holder expanding the plug into relatively firm sealing engagement with the tube side wall structure. The holder may be uncoupled from the plug when the tube is filled with the specimen and the plug occupies the open end of the tube. The tube and its contents including the plug may be placed in a centrifuge. The plug may have a specific density intermediate those of the plasma and cell portions of the specimen and, when a centrifugal force is applied sufficient for separation of such specimen portions, the plug in seeking its own specific density level in the tube is deformed and moved downwardly in the tube. When such force is removed after such separation, the plug provides a plasma-cell barrier.

10 Claims, 7 Drawing Figures

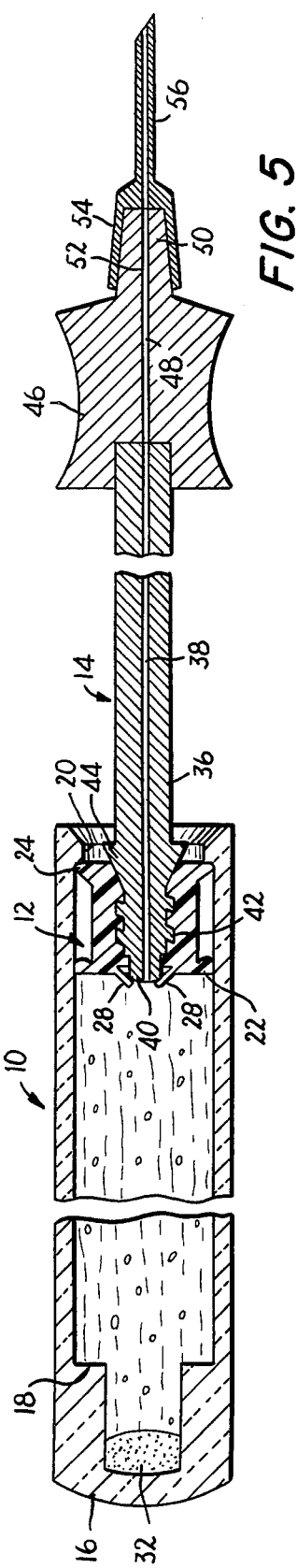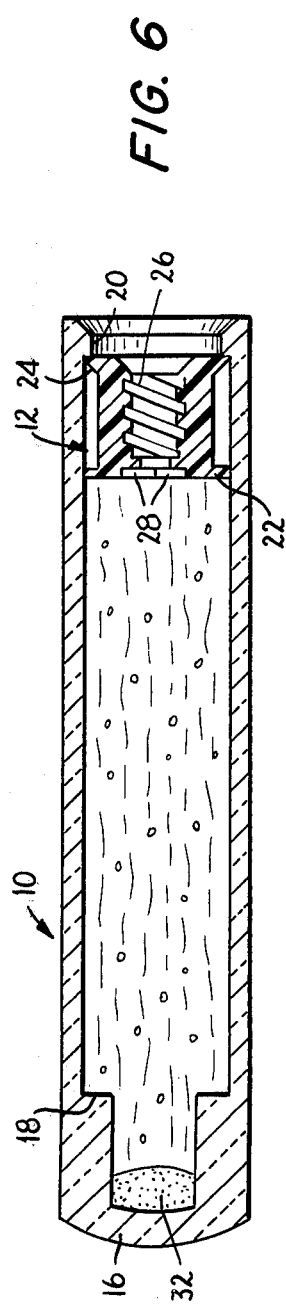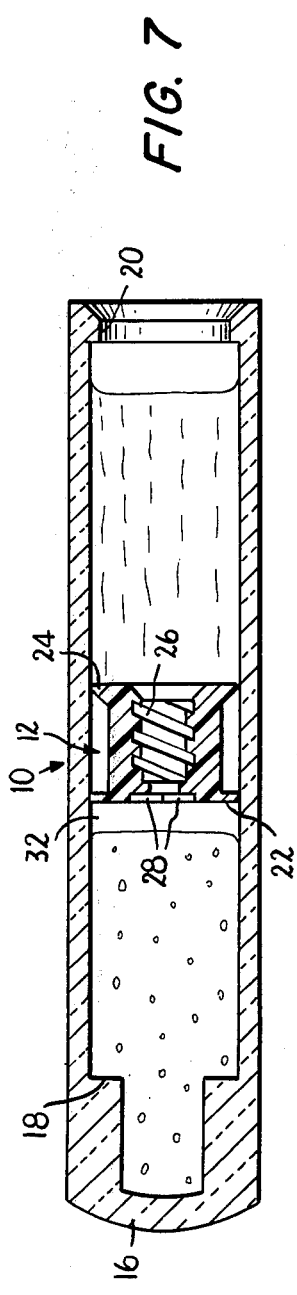

BLOOD COLLECTING SYRINGE

BACKGROUND OF THE INVENTION

1. Field of the Invention

This invention relates to a syringe of the type having a fluid-receiving tube provided with an open end and a closed end.

2. Prior Art

Heretofore, it has been proposed to provide a syringe, as in Sausse U.S. Pat. No. 3,696,806, including a fluid-receiving tube having a closed end and an open end, and a resilient plug for relative reciprocating motion in the tube while having relatively firm sealing engagement with the side wall structure of the tube. The plug is connectible to a needle-carrying member which when connected extends through the normally closed plug. The needle-carrying member is operative to hold the plug stationary as the tube is manipulated thereover. It appears that when the tube is in filled condition with the plug occupying the open end of the tube, the holder may be removed from the plug, the resilient plug closing the hole therethrough previously made by the holder. The plug in this position may serve as a tube stopper. The aforementioned extension of the holder through the plug does not appreciably expand the plug as the portion of the holder which extends through the plug is only a thin hollow needle such as a hypodermic needle. The drawback of this article is that the plug sealing pressure on the tube cannot be at least partially relieved which is required, if the plug is to be displaced in the tube as as a function of a specific density thereof greater than one phase of the specimen but less than another phase of the specimen, when the specimen in the tube is centrifuged, not suggested by Sausse.

It has also been proposed, as in Sarstedt U.S. Pat. No. 3,886,928, to provide a fluid-receiving tube closed at one end and open at the other and receiving a needle or cannula holder having as a permanent part thereof an enlargement for relatively firm sealing engagement with the side wall structure with the tube. A granulated material between the enlargement and the bottom of the tube has a specific density intermediate those of a plasma portion and a cell portion of a drawn blood specimen. After such a blood specimen is drawn, the holder may be removed from the tube and the tube placed in a centrifuge to separate the aforementioned portions of the blood specimen. Such separation is effective to place the aforementioned substance of intermediate specific density between such specimen portions as a barrier. However, such barrier has the defect that it does not include a performed plug. While the Sarstedt patent does not disclose a cannula adapter separable from the aforementioned holder and having a valve therein to stop the flow of blood from the donor while the cannula remains injected into a vein in the donor and the holder is disconnected from the adapter, this provision has been made in practice. The provision permits one tube and holder assembly to be exchanged for another with reference to the cannula adapter while the cannula remains injected in the donor for drawing multiple tubes of blood from the donor.

It has also been proposed in an article for collecting blood specimens to provide an evacuated tube having a plug in an open end thereof and having a closed end. According to one aspect of the proposal, a blood specimen is caused to flow through a double-ended needle extended at one end into a vein of the donor and extended at the other end through the plug. After the specimen fills the tube, the needle is removed from both the donor and the plug, and the tube and its contents are subjected to a centrifugal force sufficient to separate the plasma and cell portions of the specimen. Thereafter an additional centrifugal force is applied to displace the plug to a barrier position intermediate the plasma and cell portions, the plug having a specific density intermediate those of the aforementioned specimen portions.

An evacuated blood collection device has the disadvantage that the initial vacuum in the tube may cause the collapse of an injected vein which has reduced elasticity such as caused, for example, by certain types of ill health or advanced age. Evacuated blood collection devices have been known to lose their usefulness as such collection devices by the loss of at least partial vacuum while in storage. Perhaps, the most serious disadvantage of these evacuated devices is that the user does not have any control over the degree of vacuum applied the vein at any time during the collection of a blood specimen. The control is lacking which the user normally has in the use of a conventional syringe, including a piston in a barrel or tube which is manipulated by the user, to create the desired degree of vacuum to draw a blood specimen. The prior art also discloses an alternative technique of filling a tube with a specimen in a manner not requiring the aforementioned evacuated condition of the tube. However, if this technique is used, the tube must be filled from another vessel and the plug is usually positioned in the tube after the filling operation. This manner of use leads to risk of contamination of the specimen and possible loss of identity of the origin of the specimen.

The present invention overcomes these difficulties in prior art specimen collection devices.

SUMMARY OF THE INVENTION

One object of the invention is to provide an improved syringe. Another object is to provide a syringe of the type in which vacuum is created therein by manipulation of parts thereof, the syringe having parts which may be disassembled and discarded after drawing the specimen so that the remaining parts with the drawn speciment specimen be placed in a centrifuge for separation of the lighter and heavier phases of the specimen, with a part of the device common to the syringe forming a barrier between such separated lighter and heavier phases. Still another advantage of the device is that it includes a tube which after centrifugation of the specimen therein in the aforementioned manner may be placed in an automatic machine for withdrawal of the upper or lighter specimen phase for analysis in such machine of one or more constituents of such lighter phase.

In accordance with the invention there is provided a device for drawing a blood specimen comprising a specimen-receiving tube having a closed end and an open end and a resilient expandable plug received in the closed end portion of the tube in normally unexpanded relatively light sealing engagement with a side wall structure of the tube. The device further includes an elongated cannula holder having a through longitudinal passageway for communication with the interior of the cannula, the plug and the holder having coacting means releasably coupling the plug and the holder when the holder passageway is in communication with the closed end portion of the tube through the plug, the holder expanding the plug into relatively firm sealing engagement with the tube side wall structure, so that on relative movement of the holder and the tube a specimen may be drawn into the tube.

BRIEF DESCRIPTION OF THE DRAWINGS

In the drawings:

FIG. 5 is a view similar to FIG. 2 but illustrating the syringe filled with a blood specimen;

FIG. 6 is a view similar to FIG. 5 but illustrating the remaining portion of the filled syringe after disassembly and removal of the cannula holder; and FIG. 7 is a view similar to FIG. 6 but illustrating the remaining portion of the filled syringe after centrifugation of same.

DETAILED DESCRIPTION OF THE PREFERRED EMBODIMENTS

The general organization of the major parts of the syringe includes a specimen-receiving tube indicated generally at 10, an expandable resilient plug in the tube and indicated generally at 12, and a cannula holder having a through passageway and indicated generally at 14, which holder is capable of being releasably coupled to the plug 12 and capable of expanding the plug into relatively firm sealing contact with the side wall structure of the tube 10 to form a piston so that, when thusly coupled and expanded, on movement of the tube relatively to the holder in the appropriate direction a specimen may be drawn into the tube through the cannula holder 14 then in fluid communication with the closed end portion of the tube through the plug 12.

Figure 3:
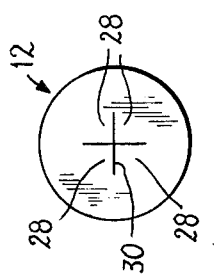
FIG. 3 is a bottom view of the plug of the assembly.
Figure 1:
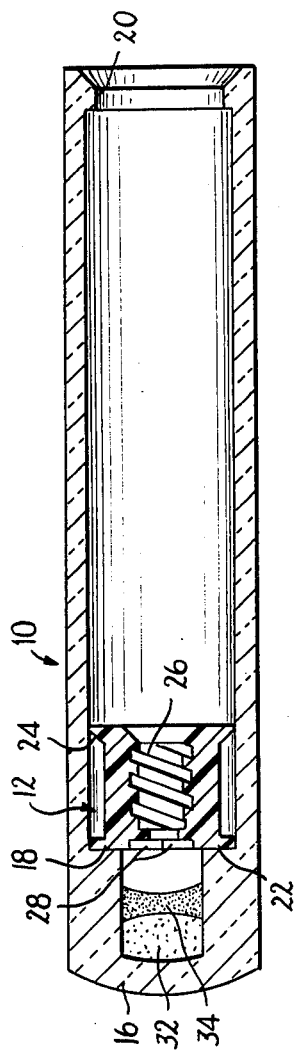
FIG. 1 is a median sectional view of a portion of a syringe assembly embodying the invention.
Figure 4:
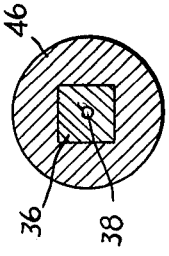
FIG. 4 is a sectional view taken on line 4—4 of FIG. 2.

The tube 10 of glass or plastic material has an open outer end and a closed inner end 16, and adjacent the closed end portion of the tube the side wall structure defines an internal annular shoulder 18 facing the open tube end. Adjacent the open end, the tube has an internal annular bead 20. The plug 12, formed of resilient rubber-like material which may be plastic, has the cross sectional form best shown in FIGS. 1 and 3 and may be inserted in the tube by being deformed sufficiently to pass the bead 20. The plug is held captive in the tube between the shoulder 18 and the bead 20 and is normally located in abutment with the shoulder 18 which prevents the plug from bottoming in the tube. The plug has an inner, integral, thin radial flange 22. The flange 22, because of its thinness, is more flexible than the body of the plug and quite susceptible to deformation. The plug 12 has an outer annular bead 24. When the plug 12 is in the normal, unexpanded condition, the plug has relatively light sealing pressure against the tube side wall structure in the areas of the flange 22 and the bead 24.

As previously indicated, the plug has a releasable coupling to the holder 14, and for this purpose the plug may have an axial bore which is internally threaded as at 26. This bore is normally closed at one end by flap portions 28 of the plug formed by a cross cut 30 in the bottom of the plug best shown in FIG. 3.

The plug 12 is structured of a material or materials giving it a specific density intermediate the specific density of a serum or plasma phase and the specific gravity of a cell phase of a blood specimen. Prior to assembly of the plug 12 with the tube 10, a semi-liquid sealant 32 including silicone oil may be located in the tube bottom (FIG. 1), the sealant having a specific density the same as the plug 12. As also shown in this view, a suitable anticoagulant 34 may be placed in the tube prior to assembly of the plug. If it is desired to separate for analysis a blood specimen into serum and cell phases the anticoagulant is omitted. On the other hand, if no separation of a blood specimen is required and it is desired to utilize for analysis a specimen of whole blood, the anticoagulant 34 is omitted.

Figure 2:
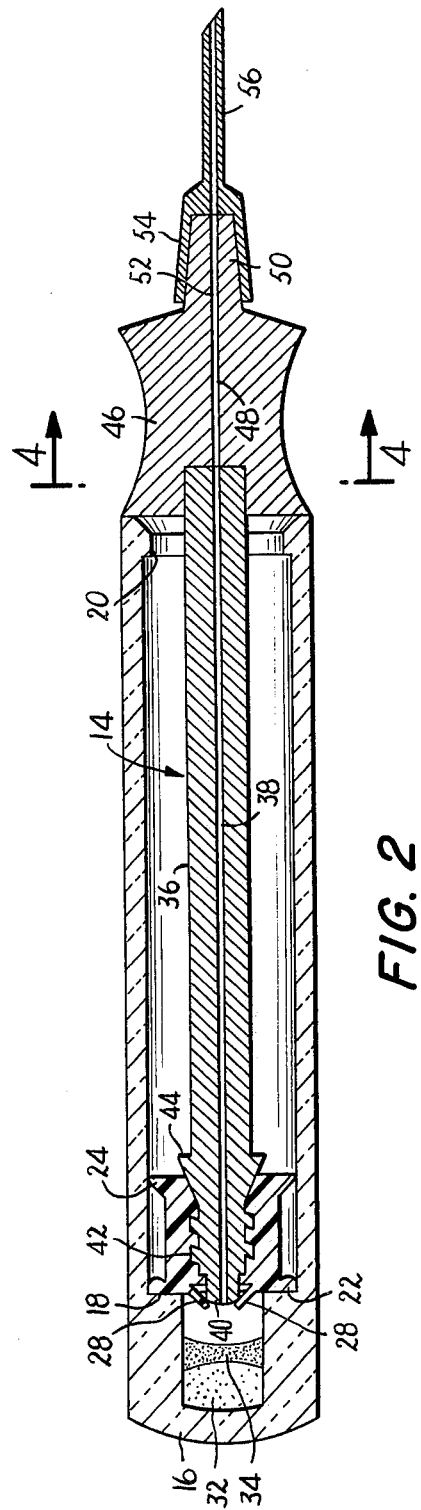
FIG. 2 is a similar sectional view illustrating the complete syringe assembly.

The holder 14 comprises a longitudinal section 36 of square cross section for example, formed of a suitable stiff plastic material and having an axial bore 38 therethrough. The section 36 has a reduced inner end portion 40 and outwardly thereof an externally threaded portion 42 to cooperate with the internally threaded portion 26 of the plug. Outwardly of the threaded portion 42, the section 36 has an enlargement 44 of cylindrical cross section of truncated conical shape which coacts with the internal bore of the plug to expand the plug when the holder is coupled to the plug in the manner shown in FIG. 2. On coupling of the holder and the plug, the reduced end 40 of the holder is extended through the plug bore in a manner to contact and open the normally closed plug flaps 28 so that the holder bore 38 is placed in fluid-flow communication with the closed end portion of the tube 10. In such coupled and expanded condition, the plug 12 is in relatively firm sealing condition with the side wall structure of the tube and the plug is deformed to the extent shown in FIG. 2 by such sealing contact.

The structure of the holder 14 is such that the other end of the holder section 36 is permanently fixed in a complementally shaped socket in one end of a resilient, generally spool-shaped part 46 having an axial bore 48 aligned with the bore 38. The holder section 36 may be cemented in the socket of the member 46, the connection being such that the holder section 36 may be moved angularly with the member 46 when the latter is grasped to thread the section 36 into the plug 12. The member 46 is grasped between the thumb and the forefinger of a user's hand on use of the syringe to draw a specimen by relative movement of the expanded, coupled plug 12 in the tube 10 toward the open end of the latter. The structure of the holder 14 is also such that at the other end of the spool-like member 46 there is a shaft portion 50 having an axial bore 52 therethrough aligned with the bore 48 and forming an adapter portion for a thrust connection to the adapter portion 54 of an integral cannula 56 for internal communication with the bore 38.

The syringe is supplied to the user unassembled to the extent that the cannula holder 14 is not assembled with the plug 12 in the tube 10. In use, the holder 14 is inserted into the tube 10 in a manner to couple the holder to the plug 12 and expand it, all as previously described. The syringe is then assembled and ready for use in drawing a specimen. For example, the cannula 56 is inserted in a vein of a blood donor while the holder 14 and tube 10 are in the relative positions shown in FIG. 2. The user then grasps the spool-shaped member 46 of the holder in one hand and the tube 10 in the other and manipulates these parts to draw the tube 10 with respect to the holder, thereby drawing blood from the vein into the closed end portion of the tube. When the tube is filled with a specimen, the plug 12 occupies a position in abutment with the bead 20 in the open end of the tube. When in this position, the plug 12 may be drawn firmly against the bead 20 by the holder 14 so as to enable the holder 14 to be unthreaded from the plug 12 without rotation of the latter. It will be apparent that in the previously described assembly of the holder 14 with the plug 12, the plug 12 may be thrust firmly against the shoulder 18 of the tube by the holder to prevent rotation of the plug.

If a single tube of blood is all that is required for analysis, the cannula 56 may be removed from the vein prior to disassembly of the holder 14 from the plug 12. If not, the cannula 56 coupled to the holder is left in the vein while the holder is held stationary and the tube 10 is rotated to unthread the holder from the plug 12 from which the tube is removed with its contents and with the plug 12 forming a stopper. Another tube and plug assembly may then be assembled with the cannula holder by threading the tube and plug assembly on the holder while the manipulating member 46 is pinched to close off the bore 48 and prevent any flow of blood from the donor through the end 40 of the holder. In this manner as many tubes of blood may be drawn from the donor as required for analysis. If whole blood is desired for analysis, the plug 12 may be withdrawn from its stopper position in the tube 10 by the insertion of a suitable implement in the bore of the plug and the application to the plug of sufficient force to deform the plug to pass the bead 20 if the tube. Thereafter, the tube containing the specimen may be placed in an automatic machine withdrawing a portion of the specimen from the tube, as with a probe, and subsequently analyzing such sampled portion of the specimen for constituents of interest.

If the specimen requires separation into a blood serum or plasma phase and a cell phase, the tube, with the plug in the stopper position thereof, may be placed in a centrifuge and sufficient centrifical applied to separate the aforementioned portions of the specimen. In such separation of the specimen, the plug becomes located intermediate the cell portion and the plasma portion by reason of its specific density. When the sealant 32 is employed in the tube with the plug 12, the sealant becomes located in sealing relation to the cross section of the tube in abutment with the inner end of the plug 12 on such phase separation as shown in FIG. 7. The plug and sealant together form an effective physical and chemical barrier in the centrifuged specimen between the lighter and heavier phases of the specimen, namely the serum or plasma portion and the cell portion. In the separation of the specimen in a centrifuge as aforesaid, the centrifugal force which is applied is sufficient to move the plug 12, which is then in its unexpanded condition and in only relatively light sealing engagement with the tube, downwardly in the tube with at least flow of some of the lighter or plasma phase upwardly around the plug. During this downward movement of the plug with the specimen flow around the latter, the plug flange 22 is deformed as in the annular plug bead 24. Further, during this movement, the plug flaps 28 open to provide a controlled vent through the plug bore. This controlled vent may serve as a filter to entrap fibrin below the plug. Subsequent to the separation of the lighter and heavier phases of the specimen in the tube 10, the tube may be placed in an automatic machine for sampling, as with a probe, the upper or lighter phase of the specimen in the tube and automatic analysis of constituents of such phase of the specimen.

While only one form of the syringe has been illustrated and described, it will be apparent, especially to those versed in the art, that the syringe may take other forms and is susceptible to various changes in details without departing from the principles of the invention.

What is claimed is:

1. An article for drawing a blood specimen, comprising: a specimen-receiving tube having a closed end and an open end, a resilient expandable plug receivable in said tube, said plug being in normally unexpanded light sealing contact with the side wall structure of said tube, a cannula, an elongated cannula holder having a through longitudinal passageway for communication with the interior of the cannula, said plug and said holder having coacting means releasably coupling said plug and said holder with said passageway in communication with said closed end portion of said tube, said holder expanding said plug into firm sealing contact with the side wall of the tube, and inwardly extending lower and upper members adjacent said lower and upper ends, respectively, of said tube for contacting the lower and upper surfaces of said plug during the coupling and decoupling, respectively, of said plug and said holder.

2. An article as defined in claim 1, wherein: said plug has a normally closed opening therethrough which is opened by receipt therein of said holder when said holder is coupled to said plug.

3. An article as defined in claim 1, wherein: said plug has a specific density intermediate plasma and cell phases of said specimen, said plug being displaceable to a barrier position intermediate said phases on the application to said specimen in said tube of centrifugal force.

4. An article as defined in claim 1, wherein: said menas releasably coupling said holder and said plug comprises an internal thread on said plug and external thread on said holder.

5. An article as defined in claim 1, wherein: said holder comprises a wedge-shaped portion received internally of said plug and expanding said plug.

6. An article as defined in claim 1, wherein: said plug has a portion intermediate ends thereof which portion is of reduced cross section.

7. An article as defined in claim 1, wherein: said plug has an annular bead and a relatively thin circumferential flange spaced axially from said bead.

8. An article as defined in claim 1, wherein: said plug has a vent opening therethrough which is normally closed when said holder and said plug are uncoupled.

9. An article as defined in claim 1, wherein: said tube an said plug have coacting means preventing said plug from bottoming in said closed tube end.

10. An article as defined in claim 9, wherein: said plug has a specific density intermediate plasma and cell phases of said specimen, and further including a semi-liquid sealant disposed intermediate said closed tube end and said plug and normally spaced from said plug, said sealant having a specific density intermediate said plasma and cell phases, said plug and said sealant being displaceable to a barrier position intermediate said phases on the application to said specimen in said tube of centrifugal force.

* * * * *